United States Patent [19]

Hilgers et al.

[11] Patent Number: 5,026,546
[45] Date of Patent: Jun. 25, 1991

[54] STABILIZED ADJUVANT SUSPENSION COMPRISING DIMETHYL DIOCTADECYL AMMONIUM BROMIDE

[75] Inventors: Lucas A. T. Hilgers; Marinus W. Weststrate, both of Weesp, Netherlands

[73] Assignee: Duphar International Research B.V., Weesp, Netherlands

[21] Appl. No.: 134,046

[22] Filed: Dec. 17, 1987

[30] Foreign Application Priority Data

Dec. 19, 1986 [NL] Netherlands ................. 8603232

[51] Int. Cl.$^5$ .................. A61K 39/39; A61K 31/78; A61K 47/14; A61K 47/32
[52] U.S. Cl. ........................... 424/88; 424/89; 424/90; 424/91; 424/92; 424/93; 424/486; 424/487; 514/2; 514/8; 514/10; 514/12; 514/642; 514/742
[58] Field of Search ............... 424/85.8, 86, 87, 88, 424/89, 90, 91, 92, 486, 487; 514/2, 8, 21, 492, 642, 742

[56] References Cited

PUBLICATIONS

Van Houte et al., Immunology, 43, 627–634, (1981).
Snippe et al., Immunology, 39, 399–405, (1980).
Norimov et al., Biol. Abs., 78(8), Abs, 62153, (1984).
Norimov et al., Biol. Abs., 78(1), Abs. 3597, (1984).

*Primary Examiner*—Margaret Moskowitz
*Assistant Examiner*—Jeff Kushan
*Attorney, Agent, or Firm*—Stevens, Davis, Miller & Mosher

[57] ABSTRACT

A stabilized aqueous adjuvant suspension of dimethyl dioctadecyl ammonium bromide stabilized with at least 0.1 part by weight of a polymer of acrylic acid cross-linked with polyallyl sucrose per part by weight of dimethyl dioctadecyl ammonium bromide, plus a method of stabilizing vaccines adjuvanted with such dimethyl dioctadecyl ammonium bromide.

4 Claims, No Drawings

STABILIZED ADJUVANT SUSPENSION COMPRISING DIMETHYL DIOCTADECYL AMMONIUM BROMIDE

The invention relates to a new adjuvant based on dimethyl dioctadecyl ammonium bromide (DDA).

It is known that DDA is an excellent adjuvant for various vaccines. However, a disadvantage of the use of DDA is its poor solubility in water, suspensions of DDA are not stable in water, flocculate rapidly and cannot be restored by shaking.

It was found that suspensions comprising DDA can be stabilised by means of the water-soluble polymers of acrylic acid crosslinked with polyallyl sucrose, which are commercially available under the name of Carbopol. Carbopol is also known to have adjuvant properties.

By using at least 0.1 part by weight of Carbopol per part by weight of DDA, preferably at least 0.5 and very much in particular at least 1 part by weight of Carbopol per 1 part by weight of DDA, stable suspension of the adjuvant DDA are obtained.

Moreover, this stable suspension sometimes proves to have a synergetically better adjuvant activity with respect to the two individual adjuvants DDA and Carbopol.

The stability of suspensions of DDA in water, whether or not in the presence of Carbopol can be determined by incubating various mixtures at 37° C. and measuring the formed quantity of precipitate at various instants.

Suspensions of DDA in water without Carbopol comprise a precipitate already after one day. On the contrary, no precipitate can be observed after one day and after a fortnight in the DDA suspensions which comprise 1 or more parts by weight of Carbopol per part by weight of DDA. A small quantity of precipitate is present in suspensions which comprise less than 0.5 part by weight to Carbopol per part by weight of DDA after incubating for a fortnight. Suspensions of DDA comprising at least 1 part by weight of Carbopol per part by weight of DDA comprise a small quantity of precipitate only after 2 months' incubation which can be resuspended easily by shaking.

Mixtures comprising 1 mg of DDA and 2 mg of Carbopol per ml of suspension do not yet comprise any precipitate after autoclaving at 127° C. for 20 minutes.

The adjuvant activity of the Carbopol-stabilised suspensions of DDA is not attacked either by incubation at 37° C. for 2 months or autoclaving at 127° C. for 20 minutes.

The Carbopol-stabilised suspensions of DDA in water are so stable that after centrifuging for 30 minutes at a speed of 5,000 rpm (3000 g) they comprise only very little precipitate which can be resuspended by shaking.

Repeated freezing and thawing of the Carbopol-containing DDA suspensions has no influence on the stability of the suspension and does not cause precipitate.

We claim:

1. A stabilized aqueous adjuvant suspension comprising dimethyl dioctadecyl ammonium bromide stabilized with at least 0.1 part by weight of a polymer of acrylic acid crosslinked with polyallyl sucrose per part by weight of dimethyldioctadecyl ammonium bromide.

2. In a method of stabilizing vaccines adjuvanted with dimethyldioctadecyl ammonium bromide, the improvement comprising stabilizing the adjuvant solution through addition of at least 0.1 part by weight of a polymer of acrylic acid with polyallyl sucrose per part by weight of dimethyl dioactadecyl ammonium bromide.

3. A suspension as claimed in claim 1 further comprising approximately 1 part by weight of a polymer of acrylic acid crosslinked with a polyallyl sucrose per part by weight of dimethyl dioactadecyl ammonium bromide.

4. A suspension as claimed in claim 1 further comprising 0.1 mg of dimethyl dioctadecyl ammonium bromide and 0.1 mg of a polymer of acid crosslinked with polyallyl sucrose per ml of aqueous suspension.

* * * * *